United States Patent
Zhou et al.

(10) Patent No.: US 11,401,536 B2
(45) Date of Patent: Aug. 2, 2022

(54) D-PSICOSE PRODUCTION USING PROBIOTIC MICROORGANISMS

(71) Applicant: NGEE ANN POLYTECHNIC, Singapore (SG)

(72) Inventors: Xingding Zhou, Singapore (SG); Ling Jie Stephanie Lee, Singapore (SG)

(73) Assignee: NGEE ANN POLYTECHNIC, Singapore (SG)

(*) Notice: Subject to any disclaimer, the term of this patent is extended or adjusted under 35 U.S.C. 154(b) by 0 days.

(21) Appl. No.: 17/059,870

(22) PCT Filed: May 31, 2018

(86) PCT No.: PCT/SG2018/050269
§ 371 (c)(1),
(2) Date: Nov. 30, 2020

(87) PCT Pub. No.: WO2019/231393
PCT Pub. Date: Dec. 5, 2019

(65) Prior Publication Data
US 2021/0189441 A1    Jun. 24, 2021

(51) Int. Cl.
*C12P 7/56* (2006.01)
*C12P 19/02* (2006.01)

(52) U.S. Cl.
CPC .......... *C12P 7/56* (2013.01); *C12P 19/02* (2013.01)

(58) Field of Classification Search
None
See application file for complete search history.

(56) References Cited

U.S. PATENT DOCUMENTS

| 5,801,025 A * | 9/1998 | Ohara ............ C12P 7/56 435/139 |
| 2005/0106694 A1* | 5/2005 | Green ............ C12P 7/56 435/146 |

(Continued)

FOREIGN PATENT DOCUMENTS

| CA | 1292988 C | 12/1991 |
| CN | 106480125 A | 3/2017 |

(Continued)

OTHER PUBLICATIONS

Bechtold, M., et al., "Integrated operation of continuous chromatography and biotransformations for the generic high yield production of fine chemicals", Journal of Biotechnology 124(1), 146-162 (2006).

(Continued)

*Primary Examiner* — Richard C Ekstrom
(74) *Attorney, Agent, or Firm* — Viksnins Harris Padys Malen LLP

(57) ABSTRACT

The present invention provides a method of preparing D-psicose comprising the steps of (i) providing a mixture of D-psicose and D-fructose; and (ii) contacting the mixture of D-psicose and D-fructose with a probiotic microorganism that is capable of metabolizing D-fructose but not D-psicose and capable of converting D-fructose into L-lactic acid and subjecting the microorganism to culture conditions that allow fermentative removal of D-fructose from the mixture of D-psicose and D-fructose with concomitant production of L-lactic acid. Further provided are uses of a probiotic microorganism that is capable of metabolizing D-fructose but not D-psicose and capable of converting D-fructose into L-lactic acid for fermentative removal of D-fructose from a mixture of D-psicose and D-fructose. In particular, the (Continued)

probiotic microorganism is *Lactobacillus rhamnosus* GG or *Saccharomyces boulardii*.

15 Claims, 10 Drawing Sheets

Specification includes a Sequence Listing.

(56) References Cited

U.S. PATENT DOCUMENTS

| | | | | |
|---|---|---|---|---|
| 2008/0286252 | A1* | 11/2008 | Sinnott | A23L 33/135 |
| | | | | 424/93.44 |
| 2015/0010972 | A1* | 1/2015 | Irie | C12P 7/56 |
| | | | | 435/139 |
| 2015/0320099 | A1 | 11/2015 | Hugenholtz et al. | |
| 2018/0119074 | A1* | 5/2018 | Sheppard | C12G 3/024 |
| 2019/0100779 | A1* | 4/2019 | Thongchul | C12N 1/205 |
| 2019/0127766 | A1* | 5/2019 | Ask | C12N 9/0006 |
| 2019/0169658 | A1* | 6/2019 | Thongchul | C12N 9/2411 |
| 2021/0189441 | A1* | 6/2021 | Zhou | C12P 19/02 |

FOREIGN PATENT DOCUMENTS

| | | |
|---|---|---|
| JP | 2012246254 A | 12/2012 |
| WO | 2006129954 A1 | 12/2006 |

OTHER PUBLICATIONS

Binkley, W., "The fate of cane juice simple sugars during molasses formation IV. Probable conversion of D-fructose to D-psicose", Int Sugar J. 65, 105-106 (1963).
Chattopadhyay, S., et al., "Artificial sweeteners—a review", J Food Sci Technol 51(4), 611-621 (2014).
Choi, J., et al., "Improvement in the thermostability of D-psicose 3-epimerase from Agrobacterium tumefaciens by random and site-directed mutagenesis", Applied and Environmental Microbiology 77(20), 7316-7320 (2011).
Chwastek, A., et al., "Fermentation of Red Beet Juice Supplemented with Waste Highbush Blueberry-Sucrase Osmotic Syrup as a Method of Probiotic Beverage Production", J Food Process Preserv 40(4), 780-789 (2015).
Cree, G., et al., "O-isopropylidene derivatives of D-allulose (D-psicose) and D-erythro-hexopyranos-2, 3-diulose", Canadian Journal of Biochemistry 46(8), 765-770 (1968).
Degirmenciolu, N., et al., "The Monitoring, via an In Vitro Digestion System, of the Bioactive Content of Vegetable Juice Fermented with *Saccharomyces cerevisiae* and *Saccharomyces boulardii*", J Food Process Preserv 40(4), 798-811 (2016).
Gorbach, S., et al., "Lactobacillus rhamnosus GG", The Microbiota in Gastrointestinal Pathophysiology: Elsevier, Chapter 7; 79-88. (2017).
Gruber, C., et al., "Randomized, placebo-controlled trial of Lactobacillus rhamnosus GG as treatment of atopic dermatitis in infancy", Allergy 62(11), 1270-1276 (2007).
Hossain, A., et al., "Rare sugar D-psicose protects pancreas β-islets and thus improves insulin resistance in OLETF rats", Biochemical and Biophysical Research Communications 425(4), 717-723 (2012).
Iida, T., et al., "Failure of d-psicose absorbed in the small intestine to metabolize into energy and its low large intestinal fermentability in humans", Metabolism 59(2), 206-214 (2010).
Kim, H., et al., "Characterization of an Agrobacterium tumefaciens D-psicose 3-epimerase that converts D-fructose to D-psicose", Applied and Environmental Microbiology 72(2), 981-985 (2006).
Li, C., et al., "D-Psicose 3-epimerase secretory overexpression, immobilization, and d-psicose biotransformation, separation and crystallization", Journal of Chemical Technology and Biotechnology doi: 10.1002/jctb.5360, 24 pages (2017).
Li, C., et al., "Enzymatic fructose removal from D-psicose bioproduction model solution and the system modeling and simulation", Journal of Chemical Technology and Biotechnology doi: 10.1002/jctb.5483, 32 pages (2017).
Martinez, F., et al., "Lactic acid properties, applications and production: a review", Trends in Food Science & Technology 30(1), 70-83 (2013).
Matsuo, T., et al., "D-Psicose is a rare sugar that provides no energy to growing rats", Journal of Nutritional Science and Vitaminology 48(1), 77-80 (2002).
Matsuo, T., "Inhibitory effects of D-psicose on glycemic responses after oral carbohydrate tolerance test in rats", Journal of Japanese Society of Nutrition and Food Science (Japan) 59, 191-121, 2006 [English Abstract].
Matsuo, T., et al., "Less body fat accumulation with D-psicose diet versus D-fructose diet", Journal of Clinical Biochemistry and Nutrition 30, 55-65 (2001).
Miller, B., et al., "Chromatographic analyses of the free amino-acids, organic acids and sugars in wheat plant extracts", Journal of the Science of Food and Agriculture 11(6), 344-348 (1960).
Miu, W., et al., "Recent advances on applications and biotechnological production of D-psicose", Applied Microbiology and Biotechnology 94(6), 1461-1467 (2012).
Murata, A., et al., "A novel inhibitory effect of D-allose on production of reactive oxygen species from neutrophils", Journal of Bioscience and Bioengineering 96(1), 89-91 (2003).
Park, C., et al., "Production of D-psicose from D-fructose by whole recombinant cells with high-level expression of D-psicose 3-epimerase from Agrobacterium tumefaciens", Journal of Bioscience and Bioengineering 121(2), 186-190 (2016).
Patent Cooperation Treaty, International Searching Authority, Search Report and Written Opinion for PCT/SG2018/050269, 13 pages, dated Aug. 28, 2018.
Song, Y., et al., "Strategy for dual production of bioethanol and d-psicose as value-added products from cruciferous vegetable residue", Bioresource Technology 223, 34-39, doi: http://dx.doi.org/10.1016/j.biortech.2016.10.021 (2017).
Takata, M., et al., "Neuroprotective effect of D-psicose on 6-hydroxydopamine-induced apoptosis in rat pheochromocytoma (PC12) cells", Journal of Bioscience and Bioengineering 100(5), 511-516 (2005).
Takeshita, K., et al., "Mass production of D-psicose from D-fructose by a continuous bioreactor system using immobilized D-tagatose 3-epimerase", Journal of Bioscience and Bioengineering 90(4), 453-455 (2000).
Teitelbaum, J., "Probiotics and the treatment of infectious diarrhea", The Pediatric Infectious Disease Journal 24(3), 267-268 (2005).
Van Duc Long, N., et al., "Separation of D-psicose and D-fructose using simulated moving bed chromatography", Journal of Separation Science 32(11), 1987-1995 (2009).
Wagner, N., et al., "Model-based cost optimization of a reaction-separation integrated process for the enzymatic production of the rare sugar d-psicose at elevated temperatures", Chemical Engineering Science 137, 423-435 (2015).
Yan, F., et al., "Lactobacillus rhamnosus GG: an updated strategy to use microbial products to promote health", Functional Food Reviews (Print), 4(2), 77-84 (2012).
Zhang, W., et al., "Biochemical characterization of ad-psicose 3-epimerase from Treponema primitia ZAS-1 and its application on enzymatic production of d-psicose", Journal of the Science of Food and Agriculture 96(1), 49-56 (2016).
Zhang, W, et al., "Recent advances in D-allulose: Physiological functionalities, applications, and biological production", Trends in Food Science & Technology 54,127-137 (2016).

* cited by examiner

SEQUENCE LISTING

```
<160> NUMBER OF SEQ ID NOS: 4

<210> SEQ ID NO 1
<211> LENGTH: 289
<212> TYPE: PRT
<213> ORGANISM: Agrobacterium tumefaciens

<400> SEQUENCE: 1

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
                20                  25                  30

Ile Glu Val Ala Ala His His Ile Asn Glu Tyr Ser Asp Ala Glu Leu
            35                  40                  45

Ala Thr Ile Arg Lys Ser Ala Lys Asp Asn Gly Ile Ile Leu Thr Ala
        50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
        115                 120                 125

Gly Val Glu Gly Ile Asn Gly Ile Ala Asp Phe Ala Asn Asp Leu Gly
    130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285
```

Gly

<210> SEQ ID NO 2
<211> LENGTH: 289
<212> TYPE: PRT
<213> ORGANISM: Artificial Sequence
<220> FEATURE:
<223> OTHER INFORMATION: Synthetic Construct

<400> SEQUENCE: 2

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
            20                  25                  30

Leu Glu Val Ala Ala His His Ile Asn Glu Tyr Ser Asp Ala Glu Leu
        35                  40                  45

Ala Thr Ile Arg Lys Ser Ala Lys Asp Asn Gly Ile Ile Leu Thr Ala
    50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
        115                 120                 125

Gly Val Glu Gly Ile Asn Gly Ile Ala Asp Phe Ala Asn Asp Leu Gly
    130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Cys Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly

<210> SEQ ID NO 3
<211> LENGTH: 401
<212> TYPE: PRT
<213> ORGANISM: Artificial Sequence
<220> FEATURE:
<223> OTHER INFORMATION: Synthetic Construct

<400> SEQUENCE: 3

Met Ser Asp Ser Glu Val Asn Gln Glu Ala Lys Pro Glu Val Lys Pro

```
                1               5                   10                  15
            Glu Val Lys Pro Glu Thr His Ile Asn Leu Lys Val Ser Asp Gly Ser
                        20                  25                  30

Ser Glu Ile Phe Phe Lys Ile Lys Lys Thr Thr Pro Leu Arg Arg Leu
                        35                  40                  45

Met Glu Ala Phe Ala Lys Arg Gln Gly Lys Glu Met Asp Ser Leu Arg
                        50                  55                  60

Phe Leu Tyr Asp Gly Ile Arg Ile Gln Ala Asp Gln Thr Pro Glu Asp
            65                  70                  75                  80

Leu Asp Met Glu Asp Asn Asp Ile Ile Glu Ala His Arg Glu Gln Ile
                        85                  90                  95

Gly Gly Gly Gly Gly Gly Ser Gly Gly Gly Ser Gly Gly Gly Gly
                        100                 105                 110

Ser Lys His Gly Ile Tyr Tyr Ser Tyr Trp Glu His Glu Trp Ser Ala
                        115                 120                 125

Lys Phe Gly Pro Tyr Ile Glu Lys Val Ala Lys Leu Gly Phe Asp Ile
                        130                 135                 140

Leu Glu Val Ala Ala His His Ile Asn Glu Tyr Ser Asp Ala Glu Leu
            145                 150                 155                 160

Ala Thr Ile Arg Lys Ser Ala Lys Asp Asn Gly Ile Ile Leu Thr Ala
                        165                 170                 175

Gly Ile Gly Pro Ser Lys Thr Lys Asn Leu Ser Ser Glu Asp Ala Ala
                        180                 185                 190

Val Arg Ala Ala Gly Lys Ala Phe Phe Glu Arg Thr Leu Ser Asn Val
                        195                 200                 205

Ala Lys Leu Asp Ile His Thr Ile Gly Gly Ala Leu His Ser Tyr Trp
                        210                 215                 220

Pro Ile Asp Tyr Ser Gln Pro Val Asp Lys Ala Gly Asp Tyr Ala Arg
            225                 230                 235                 240

Gly Val Glu Gly Ile Asn Gly Ile Ala Asp Phe Ala Asn Asp Leu Gly
                        245                 250                 255

Ile Asn Leu Cys Ile Glu Val Leu Asn Arg Phe Glu Asn His Val Leu
                        260                 265                 270

Asn Thr Ala Ala Glu Gly Val Ala Phe Val Lys Asp Val Gly Lys Asn
                        275                 280                 285

Asn Val Lys Val Met Leu Asp Thr Phe His Met Asn Ile Glu Glu Asp
                        290                 295                 300

Ser Phe Gly Asp Ala Ile Arg Thr Ala Gly Pro Leu Leu Gly His Phe
            305                 310                 315                 320

His Thr Gly Glu Cys Asn Arg Arg Val Pro Gly Lys Gly Arg Met Pro
                        325                 330                 335

Trp His Glu Ile Gly Leu Ala Leu Arg Asp Ile Asn Tyr Thr Gly Ala
                        340                 345                 350

Val Ile Met Glu Pro Phe Val Lys Thr Gly Gly Thr Ile Gly Ser Asp
                        355                 360                 365

Ile Lys Val Trp Arg Asp Leu Ser Gly Gly Ala Asp Ile Ala Lys Met
                        370                 375                 380

Asp Glu Asp Ala Arg Asn Ala Leu Ala Phe Ser Arg Phe Val Leu Gly
            385                 390                 395                 400

Gly

<210> SEQ ID NO 4
<211> LENGTH: 113
```

```
-continued

<212> TYPE: PRT
<213> ORGANISM: Artificial Sequence
<220> FEATURE:
<223> OTHER INFORMATION: Synthetic Construct

<400> SEQUENCE: 4

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly Gly Gly Gly Gly Ser Gly Gly Gly Gly Ser Gly Gly Gly Gly
                100                 105                 110

Ser
```

D-PSICOSE PRODUCTION USING PROBIOTIC MICROORGANISMS

FIELD OF THE INVENTION

The present invention relates generally to methods and probiotic microorganisms for D-psicose production.

BACKGROUND OF THE INVENTION

There is a growing demand for low calorie sweeteners as substitutes for sucrose or other sugars in the food and pharmaceutical industries. D-psicose, also called D-allulose, is an epimer of D-fructose. It has 70% of the sweetness of sucrose but the calorie content thereof is almost zero. D-psicose has also been suggested as a reactive oxygen species scavenger, anti-obesity agent, neuroprotective agent, amelioration agent of insulin resistance, and hence an ideal sucrose substitute.

In the industry, D-psicose is produced by D-fructose epimerization as mediated by D-psicose-3-epimerase (DPEase). The bottleneck in the industrial mass production of D-psicose lies in the separation of D-psicose from D-fructose. Therefore, there is still a need in the art for alternative methods that overcome the drawbacks of existing techniques.

SUMMARY OF THE INVENTION

The present invention satisfies the aforementioned need in the art by providing a novel approach for the production and purification of D-psicose through the use of a probiotic microorganism that is capable of metabolizing D-fructose but not D-psicose and capable of converting D-fructose into L-lactic acid, which enables easy purification of D-psicose with simultaneous production of L-lactic acid and the probiotic microorganism as value-added products.

In one aspect, the present invention relates to a method of preparing D-psicose comprising the steps of:
  (i) providing a mixture of D-psicose and D-fructose; and
  (ii) contacting the mixture of D-psicose and D-fructose with a probiotic microorganism that is capable of metabolizing D-fructose but not D-psicose and capable of converting D-fructose into L-lactic acid and subjecting the microorganism to culture conditions that allow fermentative removal of D-fructose from the mixture of D-psicose and D-fructose with concomitant production of L-lactic acid.

In various embodiments, the mixture of D-psicose and D-fructose is provided by enzymatically converting D-fructose into D-psicose by a D-psicose 3-epimerase (DPEase) [EC 5.1.3.30], D-tagatose 3-epimerase (DTEase) [EC 5.1.3.31], or a cell comprising said DPEase or DTEase.

In various embodiments, the cell comprising said DPEase or DTEase is a recombinant cell.

In various embodiments, the DPEase is of *Agrobacterium tumefaciens* origin.

In preferred embodiments, the DPEase has the amino acid sequence set forth in any one of SEQ ID NOs: 1-3.

In various embodiments, the probiotic microorganism that is capable of metabolizing D-fructose but not D-psicose and capable of converting D-fructose into L-lactic acid is of the *Lactobacillus* or *Saccharomyces* genus, preferably *Lactobacillus rhamnosus* GG or *Saccharomyces boulardii*, more preferably *Lactobacillus rhamnosus* GG.

In various embodiments, the fermentative removal of D-fructose is carried out
  (1) at a pH range between 6.5 and 7.5, preferably at pH 7.5; and/or
  (2) at an initial total concentration of D-psicose and D-fructose of 200 g/L or less, preferably 180 g/L or less.

In various embodiments, in the mixture of D-fructose and D-psicose the weight ratio of D-fructose to D-psicose is at least 1:1, preferably at least 1.5:1, more preferably at least 2:1.

In various embodiments, step (ii) is carried out under conditions and for a period of time that allows the microorganism to metabolize substantially all D-fructose from the mixture.

In various embodiments, the method further comprises the step (iii) of isolating the D-psicose, preferably by centrifugation and/or chromatography.

In another aspect, the invention relates to use of a probiotic microorganism that is capable of metabolizing D-fructose but not D-psicose and capable of converting D-fructose into L-lactic acid for fermentative removal of D-fructose from a mixture of D-psicose and D-fructose.

In various embodiments, the probiotic microorganism that is selective for D-fructose and capable of converting D-fructose into L-lactic acid is *Lactobacillus rhamnosus* GG or *Saccharomyces boulardii*, preferably *Lactobacillus rhamnosus* GG.

BRIEF DESCRIPTION OF THE DRAWINGS

The invention will be better understood with reference to the detailed description when considered in conjunction with the non-limiting examples and the accompanying drawings.

DETAILED DESCRIPTION OF THE INVENTION

Figure 1:
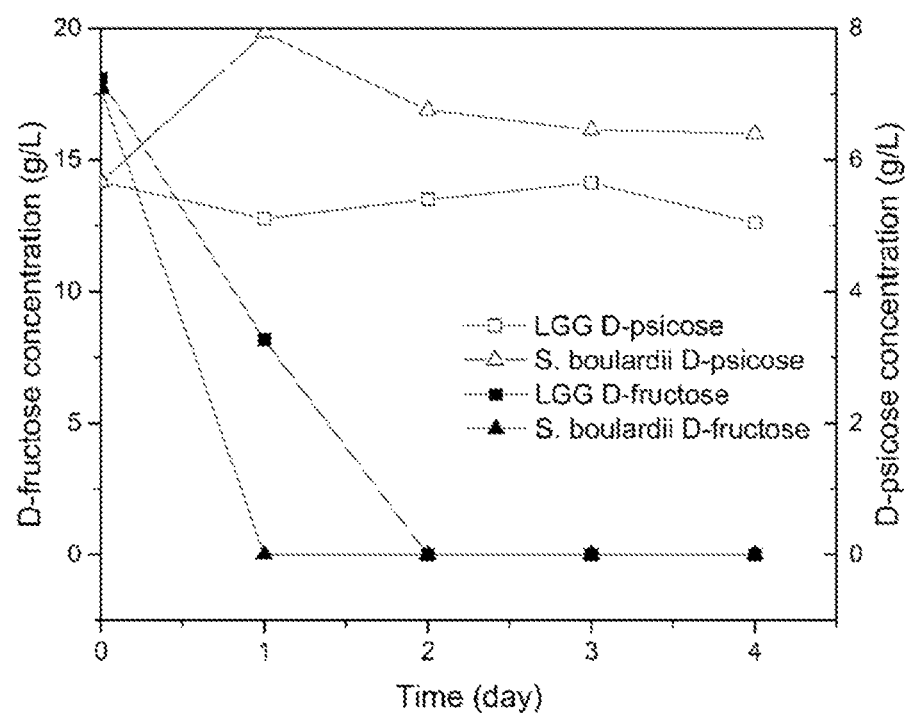
FIG. 1 shows D-fructose and D-psicose concentrations during incubation with *Lactobacillus rhamnosus* GG or *S. boulardii*. D-fructose (closed symbols), D-psicose (opened symbols), *L. rhamnosus* GG (square symbols), and *S. boulardii* (triangle symbols). Cultures were collected every 24 hours and D-fructose and D-psicose concentrations were determined by HPLC.

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

The inventors have surprisingly found that a very simple method for the separation of D-psicose from D-fructose in fermentation masses relies on the use of *L. rhamnosus* GG for bio-transformation of D-fructose into L-lactic acid. Compared to the traditional SMB method, which requires considerable amounts of investment and maintenance, this method provides a much more environmentally friendly method for purification of D-psicose. Generation of SMB is also time-consuming and labour-intensive. As disclosed herein, the separation of two sugar epimers with highly similar chemical and physical properties could be avoided and converted into separation process of sugar and an organic acid, which can be separated by technically simpler and less challenging methods than the technically and operationally challenging SMB technique.

While previous methods used include bio-transformation of the remaining D-fructose inside the DPEase enzyme reaction solution to ethanol (Song Y, et al., Bioresource technology. 2017; 223:34-9) and gluconic acid (Li C, et al., Journal of Chemical Technology and Biotechnology. 2017), for bio-transformation of D-fructose into ethanol, yeast strains like *Saccharomyces cerevisiae* are always used in fermentation process to consume D-fructose in purification of D-psicose (Song Y, et al., Bioresource technology. 2017; 223:34-9; Takeshita K, et al., Journal of bioscience and bioengineering. 2000; 90(4):453-5). However, ethanol fermentation is often unsatisfactory due to low productivity caused by the release of carbon dioxide ($CO_2$) during pyruvate transformation to ethanol. This results in loss of carbon molecules available for ethanol production therefore the maximal theoretical fructose utilization during ethanol fermentation is only about 51.1%. Furthermore, in the existing methods cruciferous vegetable residue is used for the production of D-psicose and bio-ethanol with the addition of borate to enhance the yield of D-psicose from the vegetable hydrolyzates. Since borate is toxic when consumed in large quantities, the use of this method to produce D-psicose in the food and pharmaceutical industries is limited. In another approach, Li et al. transformed D-fructose into gluconic acid by a two-step enzymatic reaction using glucose isomerase and glucose oxidase (Li C, et al., Journal of Chemical Technology and Biotechnology. 2017). However, this method required the challenging and laborious immobilization of the two enzymes to resins, with the enzyme functionality being limited by half-life and obtained final D-psicose product purities of only 91.2%, indicating the presence of significant amounts of residual D-fructose.

In contrast to these existing methods, the inventors found that by using lactic acid-producing bacteria, such as *L. rhamnosus* GG, in the purification process instead of ethanol producing microorganisms, due to high sugar utilization for lactic acid fermentation, D-fructose can be converted into L-lactic acid with a conversion rate of nearly 100% (99.3%). The high utilization rate for D-fructose during lactic acid fermentation makes it significantly more efficient than yeast ethanol fermentation.

Moreover, as disclosed herein, the need for enzyme purification and immobilization for D-psicose production could be avoided via the use of whole recombinant cells expressing DPEase or DTEase. The bio-transformation of D-fructose to L-lactic acid could also be performed by whole cell fermentation. This makes the production of D-psicose cheaper and easier to operate. Furthermore, the near-zero final D-fructose concentration after fermentation and highly efficient conversion of D-psicose to L-lactic acid shows its environmentally friendly properties. Beside D-psicose and L-lactic acid, valuable probiotic microorganisms, such as *Lactobacillus rhamnosus* GG, can be obtained, thus making this process even more cost-efficient. With its low equipment requirement and practical operation conditions, the process described herein can be easily upscaled to the industrial scale.

In one aspect, the present invention relates to a method of preparing D-psicose comprising the steps of:
  (i) providing a mixture of D-psicose and D-fructose; and
  (ii) contacting the mixture of D-psicose and D-fructose with a probiotic microorganism that is capable of metabolizing D-fructose but not D-psicose and capable of converting D-fructose into L-lactic acid and subjecting the microorganism to culture conditions that allow fermentative removal of D-fructose from the mixture of D-psicose and D-fructose with concomitant production of L-lactic acid.

In step (i) of the method disclosed herein, a mixture of D-psicose and D-fructose is provided.

The term "mixture of D-psicose and D-fructose" as used herein refers to a composition comprising, consisting of, or consisting essentially of D-psicose and D-fructose. It may further comprise other sugars or substances.

In various embodiments, the mixture of D-psicose and D-fructose is provided by enzymatically converting D-fructose into D-psicose by a D-psicose 3-epimerase (DPEase) [EC 5.1.3.30], D-tagatose 3-epimerase (DTEase) [EC 5.1.3.31], or a cell comprising said DPEase or DTEase.

The term "D-psicose 3-epimerase" or "DPEase" as used herein refers to an EC 5.1.3.30 class enzyme that has a conversion activity of D-fructose to D-psicose. The term "D-tagatose 3-epimerase" or "DTEase" as used herein refers to an EC 5.1.3.31 class enzyme that has a conversion activity of D-fructose to D-psicose. The abbreviation "EC" and accompanying notations, as used herein, are references to the enzyme classification as established by the nomenclature committee of the International Union of Biochemistry and Molecular Biology (NC-IUBMD).

The DPEase for use in step (i) of the method disclosed herein may be of any origin, preferably of *Agrobacterium tumefaciens, Pseudomonas cichorii, Clostridium* sp, *Clostridium scindens, Clostridium bolteae, Ruminococcus* sp, or *Clostridium cellulolyticum* origin, most preferably of *Agrobacterium tumefaciens* origin.

The wild-type DPEase derived from *Agrobacterium tumefaciens* has an amino acid sequence set forth in SEQ ID NO: 1.

The DPEase may be easily modified by mutagenesis conventionally known to those skilled in the art such as directed evolution and site-directed mutagenesis, etc. Therefore, it should be construed that recombinant enzymes having a certain extent of sequence homology, such as sequence homology of at least 70% or 75%, preferably at least 80% or 85%, more preferably at least 90%, 91%, 92%, 93%, 94% or 95%, most preferably at least 96%, 97%, 98%, or 99%, to any of the wild-type DPEases and being expressed as an active form may also be used in step (i) of the method disclosed herein.

Various DPEase variants known in the art, such as those disclosed in PCT Publication No. WO2013027999A9 the context of which is incorporated herein by reference, may be used for the production of D-psicose by D-psicose epimerization. In preferred embodiments, the DPEase variant with improved thermostability having the amino acid sequence set forth in SEQ ID NO:2 may be used. In more preferred embodiments, the DPEase variant with an upstream SUMO (Small Ubiquitin-like Modifier) protein having the amino acid sequence set forth in SEQ ID NO:3 may be used.

It should be noted that functional fragment of the DPEases described above may also be used for the D-fructose epimerization. The term "functional fragment" as used herein may refer to a fragment including mutations due to a substitution, an insertion or a deletion of partial amino acids in the amino acid sequence of SEQ ID NO: 1, 2, or 3 and having an activity of converting D-fructose to D-psicose.

In various embodiments, the reaction between the DPEase and D-fructose may be performed in solution.

In various embodiments, the reaction between the DPEase and D-fructose may be performed by immobilizing the DPEase on a carrier during the reaction, since DPEase immobilized on a carrier can maintain enzyme activity for a prolonged period. The carrier useful for the current embodiment of the present invention may be any of the carriers known for their use in enzyme immobilization, and may be sodium alginate, for example.

The DPEase may not be necessarily required to be purified to a high purity level, and may be used as a crude enzyme.

In various embodiments, a cell, preferably a recombinant cell, more preferably a recombinant microbial cell expressing the DPEase may be used, immobilized on a carrier or not, for the epimerization of D-fructose. Such cells may be cultured in a medium and under culture conditions that are easily selected by those skilled in the art depending on the properties of the cells. The method of culturing may include without limitation any method of culturing known to those skilled in the art, such as batch culture, continuous culture, and fed-batch culture.

The DPEase or the cell comprising the DPEase may be immobilized by any method known in the art, such as a carrier binding method, a crosslinking method, and an entrapment method.

A non-limiting example of D-psicose production by D-fructose epimerization is detailed in the present application. More examples can be found, for example, in PCT Publication Nos. WO2013027999A9 and WO/2017/150766, each of which is expressly incorporated by reference in its entirety.

One skilled in the art would readily appreciate that the above disclosure of DPEase and its use in D-psicose production also applies mutatis mutandis to DTEase.

Following epimerization of D-fructose, the key to cost-effective D-psicose production is to avoid D-fructose and D-psicose separation. Unfortunately, these two sugars share very similar structural and chemical properties, because of which separating them by current technologies e.g. column chromatography, is very expensive at the industrial scale.

A variety of methods have been applied to the separation of these two monosaccharides, like directly separating them by Simulated Moving Bed (SMB) (Li C, et al., Journal of Chemical Technology and Biotechnology. 2017) and enzyme membrane reactor (EMR) in conjugation with SMB and nanofiltration (NF) (Bechtold M, et al., Journal of biotechnology. 2006; 124(1):146-62). These methods need high investment and complex maintenance and are expensive and time-consuming.

Besides, a few indirect methods utilizing biological conversion of excess D-fructose into products easily separaable from D-psicose are also known in the art, such as fermentation with baker's yeast (Takeshita K, et al., Journal of bioscience and bioengineering. 2000; 90(4):453-5) or *S. cerevisiae* (Song Y, et al., Bioresource technology. 2017; 223:34-9). Although all of these methods are feasible for the separation of D-psicose from D-fructose, there are still some disadvantages like the wastage of almost 70% of the D-fructose when using yeast fermentation.

In step (ii) of the method disclosed herein, however, D-fructose is fermentatively removed from the mixture of D-psicose and D-fructose and converted into L-lactic acid by a probiotic microorganism, with no substantial change in D-psicose.

The term "probiotic microorganism" as used herein refers to a live microorganism which, when administered in adequate amounts, has a positive effect on the health of its host.

In accordance with the present invention, the probiotic microorganism is one that is capable of metabolizing D-fructose but substantially not D-psicose and capable of converting D-fructose into L-lactic. It should be noted that a probiotic microorganism that metabolizes D-psicose but substantially, e.g. at least 50% or 60%, preferably at least 70% or 80%, more preferably at least 90%, 95%, or 99%, less effectively than D-fructose and that is capable of converting D-fructose into L-lactic may also be considered to be suitable for the practice of the present invention in certain circumstances.

To utilize the method disclosed herein effectively for D-psicose preparation, it is critical to use culture conditions that allow the probiotic microorganism to selectively remove D-fructose from the mixture of D-psicose and D-fructose with concomitant production of L-lactic acid. The skilled person is able to determine such a favorable culture condition by consulting the application's disclosure, especially the examples, and using the knowledge known in the art.

In various embodiments, the probiotic microorganism that is capable of metabolizing D-fructose but not D-psicose and capable of converting D-fructose into L-lactic acid is of the Lactobacillus or Saccharomyces genus, preferably Lactobacillus rhamnosus GG or Saccharomyces boulardii, more preferably Lactobacillus rhamnosus GG.

Lactobacillus rhamnosus GG is a naturally occurring gram-positive bacterium originally isolated from the healthy human intestine. It has been widely used in the production of yogurt as a nutritional supplement. In the field of probiotic research, it is one of the best-studied probiotics in clinical trials. It has also been reported to exert effects on treating and/or preventing several disorders, including ulcerative colitis, diarrhea, and atopic dermatitis.

As is conventional in the art, fermentation is achieved when the probiotic microorganism is added to a medium comprising, consisting of, or consisting essentially of the mixture of D-psicose and D-fructose. Additional nutrients such as yeast extract may be required for the fermentation.

Non-limiting examples of fermentation in culture under aerobic conditions are described in the present application.

In various embodiments, in order for fermentation to proceed effectively, the fermentative removal of D-fructose is carried out (1) at a pH range between 6.5 and 7.5, preferably at pH 7.5; and/or (2) at an initial total concentration of D-psicose and D-fructose of 200 g/L or less, preferably 180 g/L or less.

In various embodiments, in the mixture of D-fructose and D-psicose the weight ratio of D-fructose to D-psicose is at least 1:1, preferably at least 1.5:1, more preferably at least 2:1.

In various embodiments, step (ii) is carried out under conditions and for a period of time that allows the microorganism to metabolize substantially all D-fructose from the mixture.

In various embodiments, the method further comprises the step (iii) of isolating the D-psicose, preferably by centrifugation and/or chromatography. Following the fermentation of step (ii), one or more post-fermentation processing steps can be used such as pasteurization, filtration, centrifugation, homogenization, and/or chromatography, as well known to those skilled in the art.

In another aspect, the invention relates to use of a probiotic microorganism that is capable of metabolizing D-fructose but not D-psicose and capable of converting D-fructose into L-lactic acid for fermentative removal of D-fructose from a mixture of D-psicose and D-fructose.

In various embodiments, the probiotic microorganism that is selective for D-fructose and capable of converting D-fructose into L-lactic acid is Lactobacillus rhamnosus GG or Saccharomyces boulardii, preferably Lactobacillus rhamnosus GG.

The present invention is further illustrated by the following examples. However, it should be understood, that the invention is not limited to the exemplified embodiments.

EXAMPLES

Materials and Methods
Microorganisms and Plasmid

E. coli BL21(DE3) strain was used as host strain for enzyme expression. A double-site mutant gene of DPEase from A. tumefaciens with a sequence coding for SUMO (Small Ubiquitin-like Modifier) protein upstream of the DPEase gene was cloned into vector pETDuet-1 between NdeI and XhoI cloning site. The final expressed enzyme was a double site variant (I33L-S213C) of DPEase from A. tumefaciens with an upstream SUMO protein, having the amino acid sequence as set forth in SEQ ID NO: 3.

L. rhamnosus GG and Saccharomyces boulardii were purchased from the American Type Culture Collection with ATCC no 53103 for LGG and ATCC no 74012 for S. boulardii.

Culture Media and Conditions

Terrific Both (TB): 2.31 g/L $KH_2PO_4$, 12.54 g/L $K_2HPO_4$, 12 g/L tryptone, 24 g/L yeast extract, 0.4% glycerol; MRS broth; Broth A: 20 g/L D-glucose, 20 g/L yeast extract and 20 g/L $CaCO_3$; Broth B: 20 g/L D-fructose, 5 g/L D-psicose, 20 g/L yeast extract and 20 g/L $CaCO_3$; Broth C: 20 g/L D-glucose, 20 g/L yeast extract, and Broth D: 20 g/L D-fructose, 5 g/L D-psicose and 20 g/L yeast extract.

Preparation of Whole Recombinant Cells with Expression of DPEase

A single colony of the recombinant E. coli was first inoculated in TB broth with 100 μg/ml ampicillin at 37° C. with 200 rpm shaking for overnight. One ml overnight culture was then sub-cultured to 100 ml fresh TB broth with 100 μg/ml ampicillin in a 500 ml flask with shaking at 200 rpm. When the optical density (OD) at 600 nm of bacterial culture reached 0.6, isopropyl-β-D-thiogalactopyranoside (IPTG) was added to a final concentration of 0.1 mM to induce DPEase expression. The culture was incubated at 16° C. with shaking at 200 rpm for 24 h to express the enzyme.

After induction was completed, the recombinant cells expressing the double-site mutant of A. tumefaciens DPEase were harvested from the culture broth by centrifugation at 6000 g for 30 mins at 4° C., and the cells were washed twice with 0.85% NaCl. The washed cells were then directly used in the production of D-psicose from 700 g/L D-fructose (pH 8.5, 20 mM Tris).

The Production of D-Psicose

The washed cells were added to 700 g/L D-fructose (20 mM Tris, pH 8.5) to a concentration of about 10 g/L, after suspension, the suspension was kept in a 55° C. incubator with shaking at 200 rpm. After overnight reaction, the supernatant was collected after centrifugation at 13000 g for 30 mins, followed by filtration through a 0.22 μm filter unit for sterilization. The final filtrate was a mixture of D-psicose (26-30% mass ratio in total sugar) and D-fructose, which was further used in the fermentation process.

Selection of Strains that can Consume D-Fructose but not D-Psicose

Various probiotic strains were firstly separately inoculated in 4 ml Broth A (20 g/L D-glucose, 20 g/L yeast extract, and 20 g/L $CaCO_3$) in 37° C. without shaking. After overnight incubation, 40 μl of the overnight culture was sub-cultured into 4 ml Broth B (20 g/L D-fructose, 5 g/L D-psicose, 20 g/L yeast extract, and 20 g/L $CaCO_3$) in 37° C. Excessive amounts of calcium carbonate was added into the broth to adjust pH thus preventing the termination of fermentation due to high media acidity. Samples were collected daily and the concentration of D-fructose and D-psicose were determined by High Performance Liquid Chromatography (HPLC).

For probiotic yeast strain S. boulardii, it was firstly inoculated overnight in 4 ml Broth C (20 g/L D-glucose, 20 g/L yeast extract) from a single colony for overnight, then 40 µl was sub-cultured into 4 ml Broth D (20 g/L D-fructose, 5 g/L D-Psicose, 20 g/L yeast extract). Samples were collected daily and the concentration of D-fructose and D-psicose were determined by HPLC.

Determination of Fermentation Conditions

The effects of total sugar concentration of the mixture of D-fructose and D-psicose on D-fructose consumption and L-lactic acid production was examined in a medium composed of 100 g/L $CaCO_3$ and 5 g/L yeast extract with a range of the total sugar concentration varying from 50 to 250 g/L in a 37° C. incubator with shaking at 200 rpm. While the effect of pH on the production of L-lactic acid was examined from pH 6.0 to 8.5 in 1 L of media composed of 100 g/L D-fructose and 20 g/L yeast extract in a 5 L Sartorius Biostat A Plus bioreactor (Sartorius Stedim), 10 M sodium hydroxide (NaOH) was used to control the pH during fermentation. Samples were collected every 4 to 6 hours to test the concentration of D-psicose and D-fructose in addition with L-lactic acid produced by using HPLC.

Separation of D-Psicose from D-Fructose by Biotransformation from D-Fructose to L-Lactic Acid Via Fermentation Lactobacillus rhamnosus GG was stored at −80° C. in a media composed of 75% culture and 25% glycerol. A seed culture was prepared by firstly streaking the glycerol stock to the MRS plates. A single colony was selected from the plate after 48 hours incubation at 37° C. and inoculated into 10 ml of MRS broth. The inoculum was incubated at 37° C. for 18 h, followed by sub-culture in 100 mL of fresh MRS broth in a 500 mL Erlenmeyer flask and shaking (200 rpm) at 37° C. for 24 h to produce a seed culture. The seed culture was then added to 1 L of fresh medium composed of 180 g/L total sugar (mixture of D-fructose and D-psicose) and 5 g/L yeast extract. The fermentation was conducted in a 5 L bio-reactor at pH 7.5 (maintained by addition of 10 M NaOH) during fermentation. Samples were taken every 4 to 6 hours to test the concentration of D-psicose, D-fructose and L-lactic acid produced using HPLC.

Analytical Methods

The concentration of D-fructose and D-psicose were determined using a HPLC system (1260 Infinity II Quaternary, Aglient Technologies, USA) equipped with a RID detector (G7162A, Aglient Technologies) and a Benson Polymeric 1000-0 BP-100 $Ca^{++}$ carbohydrate column. The column was eluted at 80° C. with water at a flow rate of 0.5 ml/min. The concentration of L-lactic acid was detected by the same HPLC system with the same RID detector and a Phenomenex Rezex RHM-Monosaccharide H+ (8%) column using a mobile phase of 12 mM $H_2SO_4$ with a flow rate of 0.5 ml/min at 80° C.

Figure 2:
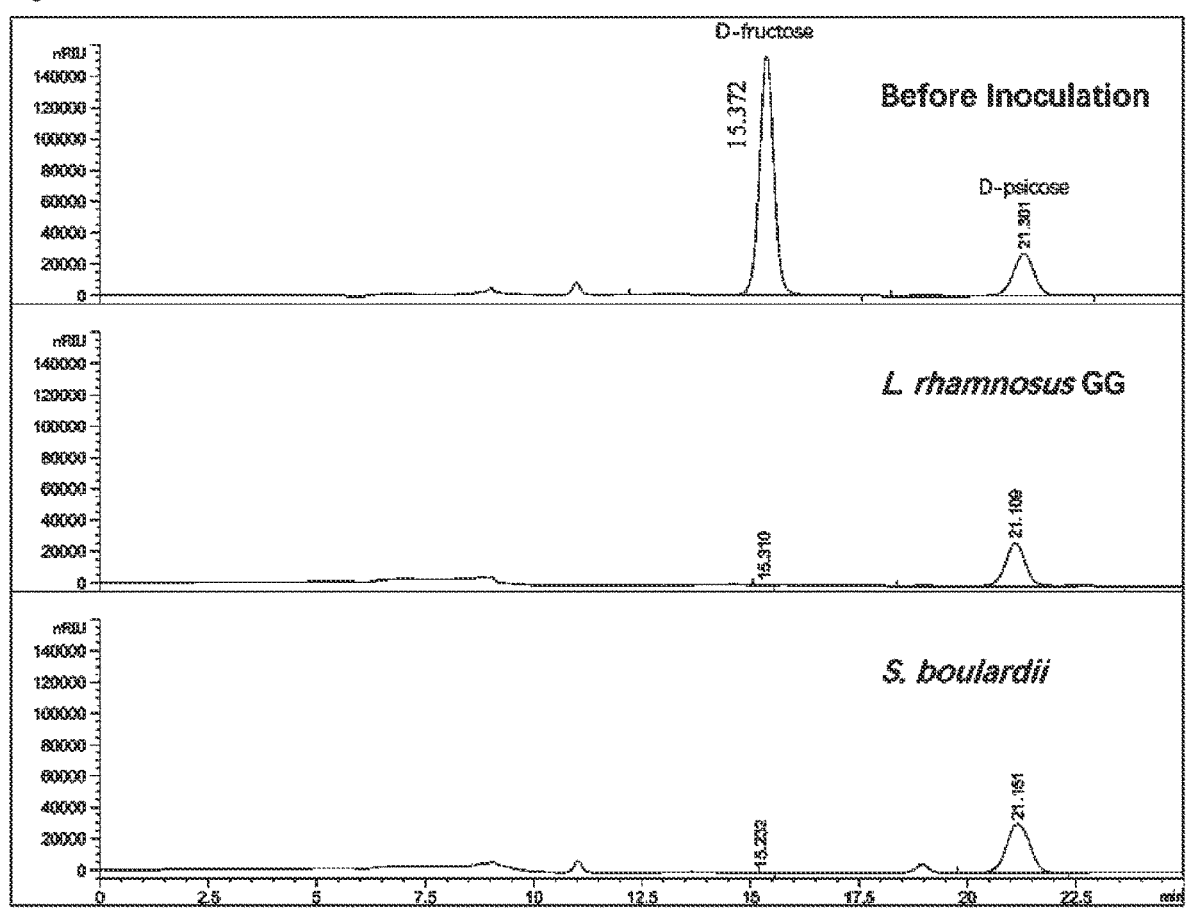
FIG. 2 shows HPLC graphs for D-fructose and D-psicose concentrations in culture before and after fermentation. The upper chart: sugar mixture of D-fructose and D-psicose before fermentation; The middle chart: 4-days incubation with *L. rhamnosus* GG; The below chart: 4-days incubation with *S. boulardii*. Data were obtained by HPLC with the Benson Polymeric 1000-0 BP-100 $Ca^{++}$ carbohydrate column.

Example 1: Selection of Microbial Strains Capable of Complete Consumption of D-Fructose but not D-Psicose Several microorganisms were tested for their abilities to utilize D-psicose and D-fructose. The results showed that 20 g/L D-fructose was utilized and could be completely consumed in 1 to 2 days by L. rhamnosus GG and S. boulardii (FIGS. 1 and 2). Moreover, the D-psicose remains unchanged.

The inventors chose L. rhamnosus GG to further investigate this new approach for D-psicose production assisted by this probiotic strain. The production of L-lactic acid using L. rhamnosus GG was subsequently optimized by varying culture conditions.

Example 2: Effect of pH on the Production of L-Lactic Acid from D-Fructose

Figure 3:
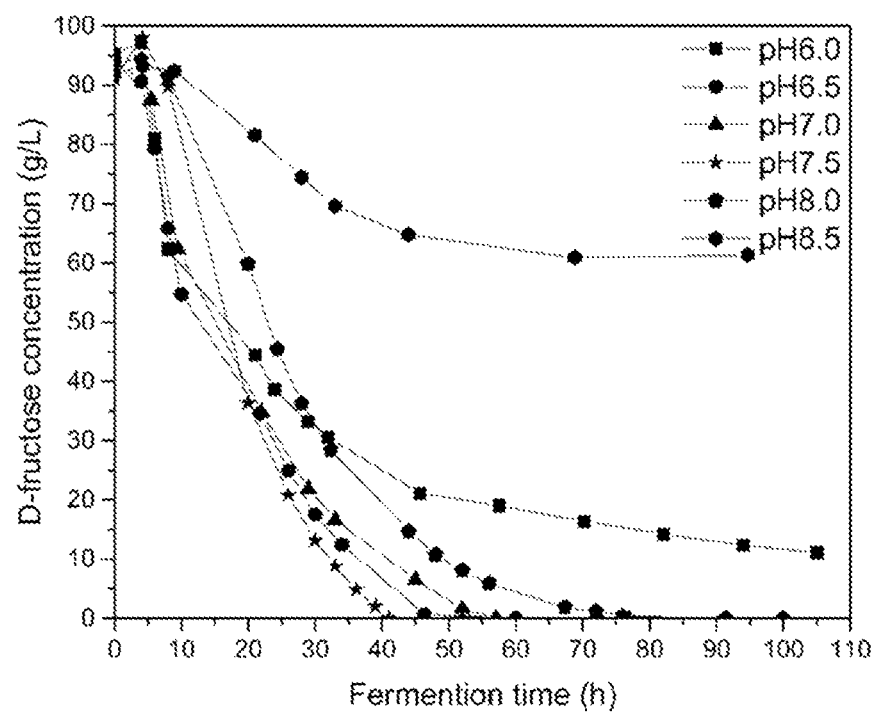
FIG. 3 shows the effect of pH on D-fructose consumption during fermentation. pH 6.0, 6.5, 7.0, 7.5 8.0 and 8.5 are represented using the square, circle, triangle, pentagram, pentagon and hexagon symbols, respectively.
Figure 4:
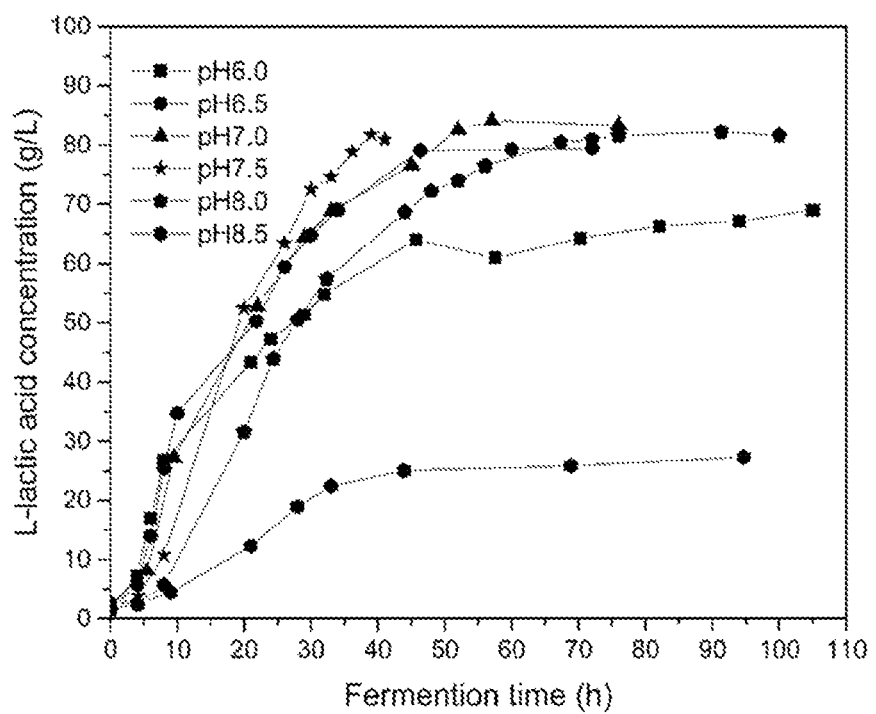
FIG. 4 shows the effect of pH on L-lactic acid production during fermentation. pH 6.0, 6.5, 7.0, 7.5 8.0 and 8.5 are represented using the square, circle, triangle, pentagram, pentagon and hexagon symbols, respectively.

The effect of pH on the production of L-lactic acid and consumption of D-fructose were assessed in a 5-L fermenter containing 1 L of culture (100 g/L D-fructose and 20 g/L of yeast extract). It can be seen that D-fructose could not be totally used up when the pH value was too low (pH 6.0) or too high (pH 8.5) even though fermentation reached 100 hours (FIG. 3), corresponding a low L-lactic acid production of around 69.1 g/L and 27.4 g/L respectively (FIG. 4). On the other hand, there were no significant differences in D-fructose consumption rates at a pH range between pH 6.5 and pH 7.5. pH 7.5 was the optimal pH at which 100 g/L fructose could be totally consumed in only 40 hours (FIG. 3). Furthermore, at pH 7.5, OD600 could reach the highest value among all conditions tested (data not shown here), indicating the highest yield for probiotic L. rhamnosus GG. Therefore, pH 7.5 was the optimal condition both for biotransformation of excessive D-fructose and probiotic production.

Figure 5:
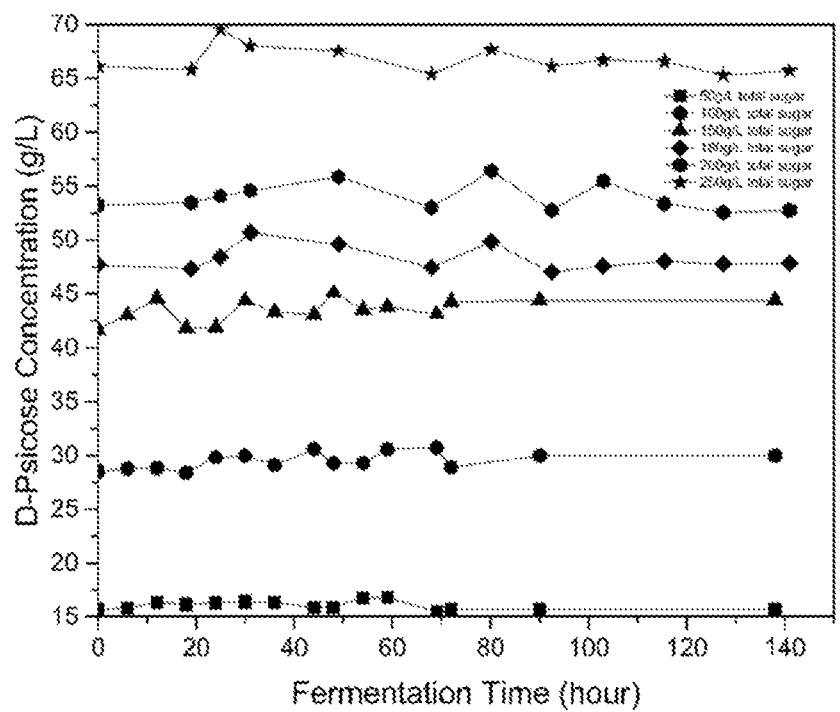
FIG. 5 shows D-psicose concentration during fermentation with various total concentrations of D-fructose and D-psicose. Symbols for the total sugar concentrations were presented in this order: 50 g/L (square), 100 g/L (circle), 150 g/L (triangle), 180 g/L (diamond), 200 g/L (hexagon) and 250 g/L (pentagram).
Figure 6:
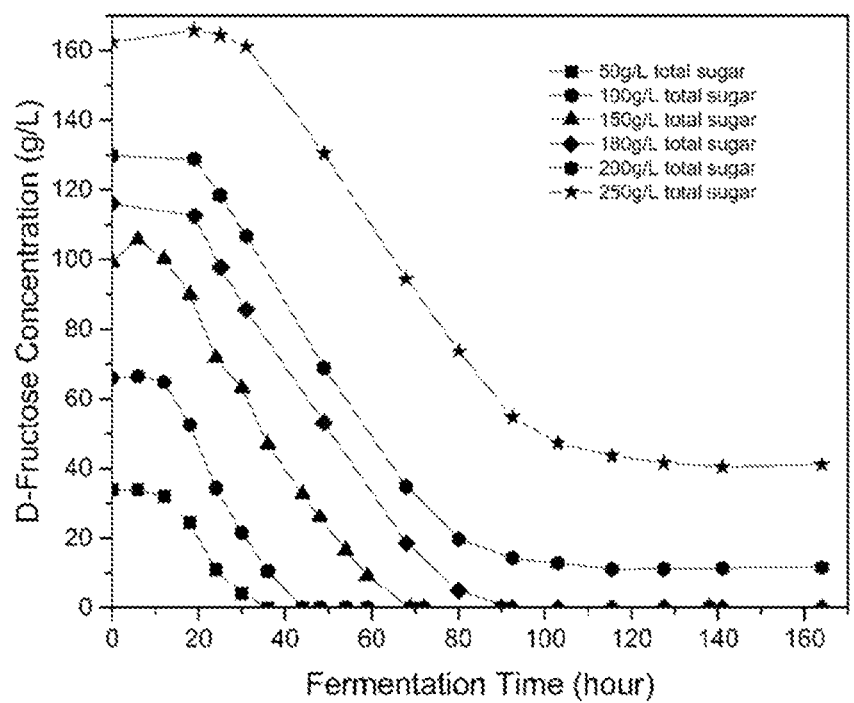
FIG. 6 shows D-fructose concentration during fermentation with various total concentrations of D-fructose and D-psicose. Symbols for the total sugar concentrations were presented in this order: 50 g/L (square), 100 g/L (circle), 150 g/L (triangle), 180 g/L (diamond), 200 g/L (hexagon) and 250 g/L (pentagram).
Figure 7:
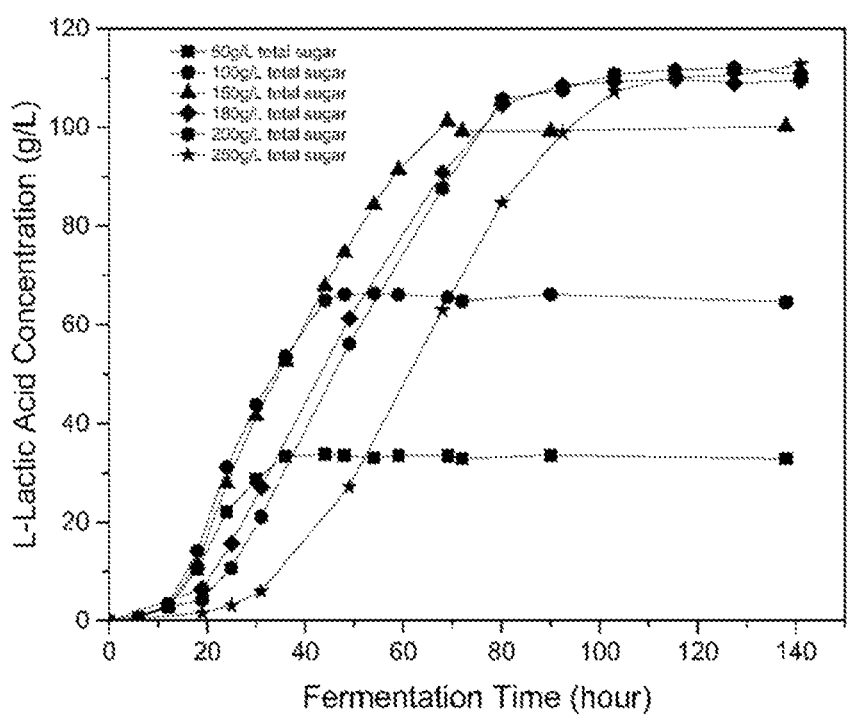
FIG. 7 shows L-lactic acid concentration during fermentation with various total concentrations of D-fructose and D-psicose. Symbols for the total sugar concentrations were presented in this order: 50 g/L (square), 100 g/L (circle), 150 g/L (triangle), 180 g/L (diamond), 200 g/L (hexagon) and 250 g/L (pentagram).

Example 3: Effect of Total Sugar Concentration of the D-Fructose and D-Psicose Mixture on D-Fructose Consumption and L-Lactic Acid Production The effect of different initial total sugar concentration in fermentation mixture, comprising D-fructose (70-74% mass fraction in total sugar) and D-psicose (26-30% mass fraction in total sugar), on the production of L-lactic acid and the ratios of D-fructose to D-psicose in fermentation masses during fermentation was evaluated (FIGS. 5 to 8). It was observed that the concentration of D-psicose remains constant (FIG. 5). Meanwhile, the concentration of D-fructose declined with various initial total sugar concentrations (FIG. 6), corresponding with a significant increase of L-lactic acid concentration (FIG. 7). Even though D-fructose could be consumed and L-lactic acid could be produced at any concentration from 50 to 250 g/L initial total sugar, the efficiency of L-lactic acid production differed greatly. At initial total concentrations below 200 g/L, D-fructose could be rapidly consumed completely with various rates of about 0.94, 1.54, 1.52 and 1.38 g/L/h for 50, 100, 150, and 180 g/L initial total sugar concentrations respectively with corresponding L-lactic acid production efficiency rates of about 1.15, 1.80, 1.52, and 1.38 g/L/h respectively. However, when the D-fructose concentration reached 200 g/L, it could not be totally utilized even after 103 hours of fermentation with a dramatically decreased consumption rate of about 1.14 g/L/h. At 250 g/L, the D-fructose inside the fermentation media could not completely consumed during fermentation with a further reduced consumption rate of about 0.88 g/L/h even after 141 hours, indicating a significant substrate inhibition.

Figure 8:
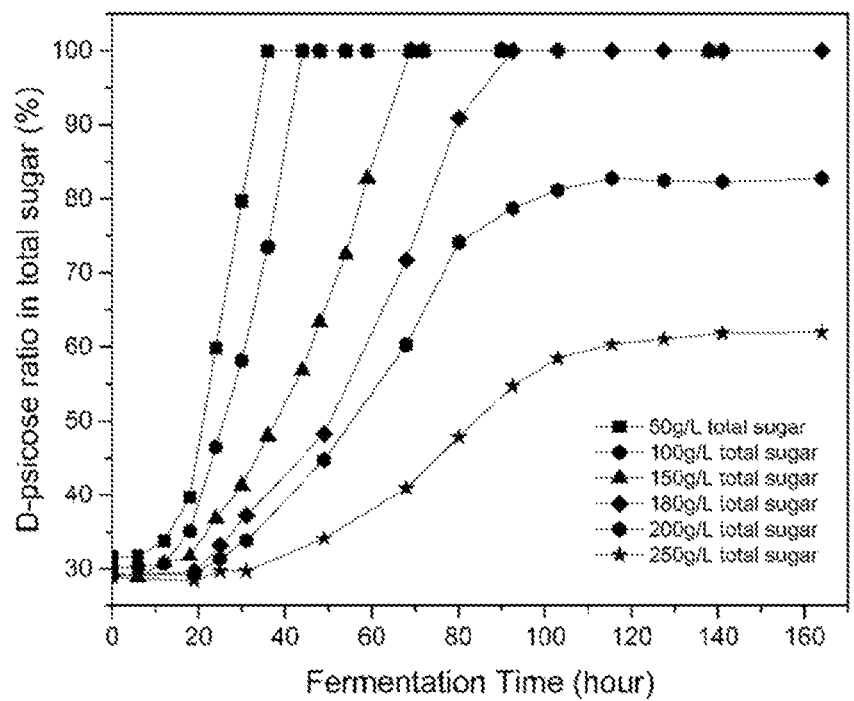
FIG. 8 shows the ratios of D-psicose in total sugar in the fermentation medium during fermentation at different initial total sugar concentrations. Symbols for the total sugar concentrations were presented in this order: 50 g/L (square), 100 g/L (circle), 150 g/L (triangle), 180 g/L (diamond), 200 g/L (hexagon) and 250 g/L (pentagram).

FIG. 8 shows the ratios of D-psicose: D-fructose in the fermentation medium during fermentation at different initial total sugar concentrations. As D-fructose was gradually consumed, the proportion of D-psicose kept increasing, and the final proportion of D-psicose in total monosaccharides inside the fermentation masses reached almost 100% in less than 85 hours when the initial total concentrations were below 200 g/L. 180 g/L initial total sugar was the optimal concentration to obtain D-psicose free of D-fructose. In contrast, D-psicose could only attain a proportion of 82.7% and 61.9% (D-psicose: D-fructose) after 141 hours fermentation with 200 g/L and 250 g/L initial total sugar concentration respectively.

Example 4: Fermentation of the Mixture of D-Psicose and D-Fructose

Figure 9:
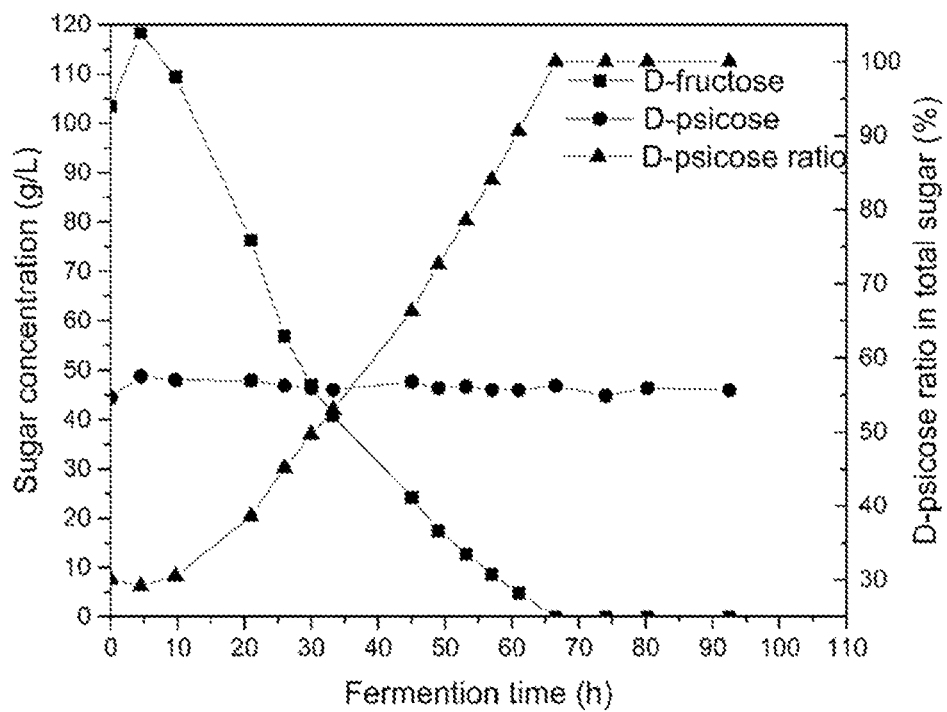
FIG. 9 shows the changes of D-psicose and D-fructose in addition with D-psicose ration during fermentation with *L. rhamnosus*. D-fructose: square, D-psicose: circle, D-psicose ratio in total sugar:triangle.
Figure 10:
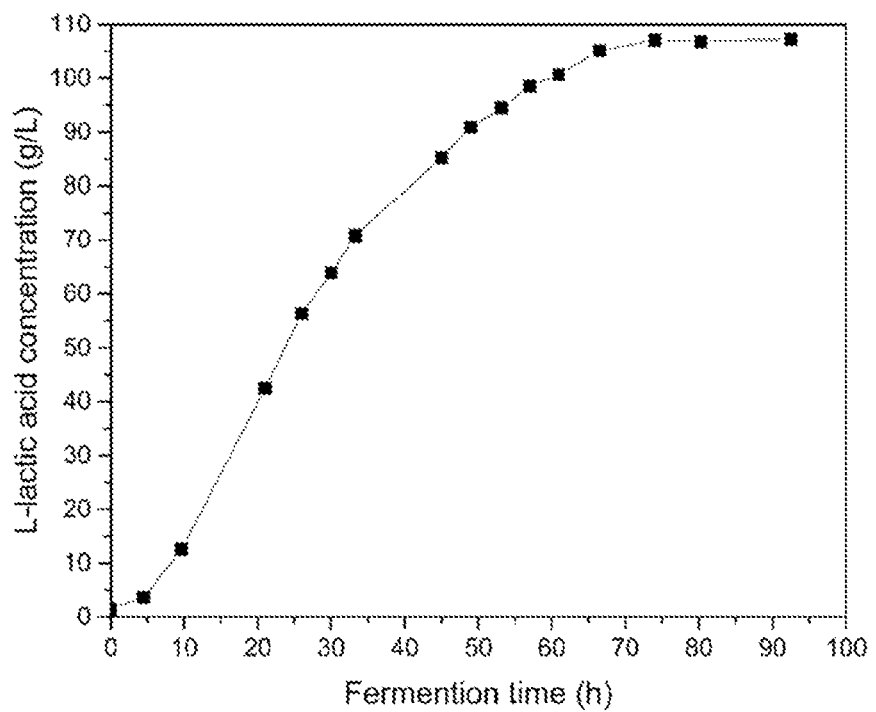
FIG. 10 shows L-lactic acid production during fermentation with *L. rhamnosus*.

Based on the effect of pH and total concentration of sugar mixture on the consumption of D-fructose and the production of L-lactic acid, a final fermentation of the sugar mixture with 180 g/L total concentration and pH 7.5 (maintained by 10M NaOH) was carried out. The concentration of D-psicose was maintained throughout fermentation while the concentration of D-fructose gradually declined until there was no more fructose remaining in the fermentation medium (FIG. 9), thus the ratio of D-psicose in total monosaccharides increased from the initial 30.1% to a final ratio of 100%. This indicated that transformation of the remaining D-fructose into L-lactic acid successfully solves the challenge of D-fructose and D-psicose separation (FIG. 10). In the end, the OD of culture reaches 12.89.

Table 1 provides details about L-lactic acid and biomass production during fermentation. In the end of fermentation, 107 g/L L-lactic acid was obtained, with a yield of 99.2%. Meanwhile, 4.6 g/L of dry weight probiotic was also obtained.

TABLE 1

Lactic acid productivity and fructose utilization rate during L-lactic acid fermentation of the D-fructose and D-psicose sugar mixture

| Initial total sugar concentration (g/L) | Fermentation time (h) | Lactic acid titer (g/L) | Lactic acid productivity (g/L) | Lactic acid yield (%) | Biomass Dry weight (g/L) |
|---|---|---|---|---|---|
| 180 | 67 | 107.3 | 1.6 | 99.3 | 4.6 |

The examples demonstrate that the probiotic strain *Lactobacillus rhamnosus* GG could be successfully used to facilitate D-psicose production. At a maximal total concentration of 180 g/L supplemented with 20 g/L yeast extract, D-fructose was rapidly and completely consumed. At pH 7.5 a yield of 107 g/L L-lactic acid could be obtained. The final fermentation mixture contains 100% pure D-psicose (relative to the amount of D-fructose/D-psicose) with L-lactate and probiotic biomass as valuable by-products.

TABLE 2

Amino acid sequences

| Name | SEQ ID NO: | Amino acid sequence |
|---|---|---|
| wild-type A. tumefaciens (ATCC 33970) DPEase | 1 | MKHGIYYSYVVEHEWSAKFGPYIEKVAKLGFDI IEVAAHHINEYSDAELATIRKSAKDNGIILTAG IGPSKTKNLSSEDAAVRAAGKAFFERTLSNVAK LDIHTIGGALHSYWPIDYSQPVDKAGDYARGVE GINGIADFANDLGINLCIEVLNRFENHVLNTAA EGVAFVKDVGKNNVKVMLDTFHMNIEEDSFGDA IRTAGPLLGHFHTGESNRRVPGKGRMPWHEIGL ALRDINYTGAVIMEPFVKTGGTIGSDIKVWRDL SGGADIAKMDEDARNALAFSRFVLGG |
| Double-mutant A. tumefaciens DPEase | 2 | MKHGIYYSYVVEHEWSAKFGPYIEKVAKLGFDI LEVAAHHINEYSDAELATIRKSAKDNGIILTAG IGPSKTKNLSSEDAAVRAAGKAFFERTLSNVAK LDIHTIGGALHSYWPIDYSQPVDKAGDYARGVE GINGIADFANDLGINLCIEVLNRFENHVLNTAA EGVAFVKDVGKNNVKVMLDTFHMNIEEDSFGDA IRTAGPLLGHFHTGECNRRVPGKGRMPWHEIGL ALRDINYTGAVIMEPFVKTGGTIGSDIKVWRDL SGGADIAKMDEDARNALAFSRFVLGG |
| Double-mutant A. tumefaciens DPEase with upstream SUMO tag | 3 | MSDSEVNQEAKPEVKPETHINLKVSDGSS EIFFKIKKTTPLRRLMEAFAKRQGKEMDSLRFL YDGIRIQADQTPEDLDMEDNDIIEAHREQIGGG GGGSGGGGSGGGGSKHGIYYSYVVEHEWSAKFG PYIEKVAKLGFDILEVAAHHINEYSDAELATIR KSAKDNGIILTAGIGPSKTKNLSSEDAAVRAAG KAFFERTLSNVAKLDIHTIGGALHSYWPIDYSQ PVDKAGDYARGVEGINGIADFANDLGINLCIEV LNRFENHVLNTAAEGVAFVKDVGKNNVKVMLDT FHMNIEEDSFGDAIRTAGPLLGHFHTGECNRRV PGKGRMPWHEIGLALRDINYTGAVIMEPFVKTG GTIGSDIKVWRDLSGGADIAKMDEDARNALAFS RFVLGG |
| SUMO tag | 4 | MSDSEVNQEAKPEVKPETHINLKVSDGSS EIFFKIKKTTPLRRLMEAFAKRQGKEMDSLRFL YDGIRIQADQTPEDLDMEDNDIIEAHREQIGGG GGGSGGGGSGGGGS |

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. Method of preparing D-psicose comprising the steps of:
   (i) providing a mixture of D-psicose and D-fructose; and
   (ii) contacting the mixture of D-psicose and D-fructose with a probiotic microorganism that is capable of metabolizing D-fructose but not D-psicose and capable of converting D-fructose into L-lactic acid and subjecting the microorganism to culture conditions that allow fermentative removal of D-fructose from the mixture of D-psicose and D-fructose with concomitant production of L-lactic acid,
   wherein the probiotic microorganism that is selective for D-fructose and capable of converting D-fructose into L-lactic acid is *Lactobacillus rhamnosus* GG.

2. The method of claim 1, wherein the mixture of D-psicose and D-fructose is provided by enzymatically converting D-fructose into D-psicose by a D-psicose 3-epimerase (DPEase) that is a member of EC 5.1.3.30, D-tagatose 3-epimerase (DTEase) that is a member of EC 5.1.3.31, or a cell comprising said DPEase or DTEase.

3. The method of claim 2, wherein the cell comprising said DPEase or DTEase is a recombinant cell.

4. The method of claim 2, wherein the DPEase is of *Agrobacterium tumefaciens* origin.

5. The method of claim 2, wherein the DPEase has the amino acid sequence set forth in any one of SEQ ID NOs:1-3.

6. The method of claim 1, wherein the fermentative removal of D-fructose is carried out at a pH range between 6.5 and 7.5.

7. The method of claim 1, wherein in the mixture of D-fructose and D-psicose the weight ratio of D-fructose to D-psicose is selected from at least 1:1.

8. The method of claim 1, wherein step (ii) is carried out under conditions and for a period of time that allows the microorganism to metabolize substantially all D-fructose from the mixture.

9. The method of claim 1, wherein the method further comprises the step (iii) of isolating the D-psicose.

10. Method for fermentative removal of D-fructose from a mixture of D-psicose and D-fructose comprising: using a probiotic microorganism that is capable of metabolizing D-fructose but not D-psicose and capable of converting D-fructose into L-lactic acid for fermentative removal of D-fructose from a mixture of D-psicose and D-fructose, wherein the probiotic microorganism that is selective for D-fructose and capable of converting D-fructose into L-lactic acid is *Lactobacillus rhamnosus* GG.

11. The method of claim 6, wherein the fermentative removal of D-fructose is carried out at an initial total concentration of D-psicose and D-fructose of 200 g/L or less.

12. The method of claim 9, wherein isolating the D-psicose is by centrifugation.

13. The method of claim 9, wherein isolating the D-psicose is by chromatography.

14. The method of claim 1, wherein in the mixture of D-fructose and D-psicose the weight ratio of D-fructose to D-psicose is selected from at least 1.5:1.

15. The method of claim 1, wherein in the mixture of D-fructose and D-psicose the weight ratio of D-fructose to D-psicose is selected from at least 2:1.

* * * * *